(12) United States Patent
Margolis

(10) Patent No.: US 7,041,261 B2
(45) Date of Patent: May 9, 2006

(54) SANITIZING SPONGE CONTAINER

(76) Inventor: Brian E. Margolis, 34 Buttonwood Rd., Voorhees, NJ (US) 08043

( * ) Notice: Subject to any disclaimer, the term of this patent is extended or adjusted under 35 U.S.C. 154(b) by 397 days.

(21) Appl. No.: 10/402,202

(22) Filed: Mar. 28, 2003

(65) Prior Publication Data

US 2004/0191141 A1    Sep. 30, 2004

(51) Int. Cl.
A61I 2/18 (2006.01)
(52) U.S. Cl. .................. 422/301; 215/231; 215/354; 206/205; 206/207
(58) Field of Classification Search .............. 422/301; 215/231, 354; 206/540, 205, 207, 208, 209, 206/210; 220/233, 235, 625
See application file for complete search history.

(56) References Cited

U.S. PATENT DOCUMENTS

| 720,471 | A | * | 2/1903 | Perley ..................... 215/231 |
| 1,676,090 | A | * | 7/1928 | Johnson ................... 422/301 |
| 1,683,888 | A | * | 9/1928 | Harrison et al. ........... 215/231 |
| 2,163,862 | A | * | 6/1939 | Wing ....................... 134/137 |
| 3,749,502 | A | | 7/1973 | Krethe |
| 4,175,671 | A | * | 11/1979 | Holl et al. ................ 220/235 |
| 4,486,389 | A | * | 12/1984 | Darnell et al. ............ 422/307 |
| 4,782,941 | A | * | 11/1988 | Freise ..................... 206/5 |
| 4,831,681 | A | | 5/1989 | Puder |
| 5,605,667 | A | * | 2/1997 | Powell, Jr. ............... 422/119 |
| 5,887,769 | A | | 3/1999 | Kidd |

OTHER PUBLICATIONS

Otres Online Store, Kitchen Sponge Sanitizer Item #O001-0SP200W, www.shopotres.com, prior art.

* cited by examiner

Primary Examiner—E. Leigh McKane
(74) Attorney, Agent, or Firm—Marvin C. Gaer

(57) ABSTRACT

Sanitizing sponge disinfectant container bowls are disclosed, which are deep enough to hold cleaning sponges completely submerged in a disinfectant fluid. These containers are equipped with lids having downward projecting shafts or rotatable screw bolts which fit into the container bowl and press down on a sponge being sanitized. The lids are of sufficient weight to hold the sponges submerged in the disinfectant fluid. The container bowls are also provided with open ribbed rates against which or between which the sponges are held to facilitate the greater exposure of the surfaces of the sponges to the disinfectant fluid for improved cleansing.

8 Claims, 4 Drawing Sheets

US 7,041,261 B2

SANITIZING SPONGE CONTAINER

FIELD OF THE INVENTION

This invention is concerned with containers for storing, sanitizing and disinfecting sponges and similar cleaning materials which may have become contaminated through use.

BACKGROUND OF THE INVENTION

Utensils and products used for cleaning in the home tend to also become contaminated through their application. Some, such as paper towels, are discarded after a single use, while others, such as sponges and mops, may be used several times before being disposed of. Used sponges, in particular, because of the nature of their irregular, porous, pitted, and moist surfaces, and their large surface to volume ratios, along with the presence of organic waste, may accumulate a large amount of infectious, toxic or noxious contaminants, including harmful bacteria and molds, which are hard to reach and are therefore hard to remove, disinfect or neutralize. If these sponges could be totally immersed in an antiseptic disinfectant fluid for a period of time between uses, they would be significantly decontaminated, thus making them safer, less infectious and extending their period of usefulness. Various sponge holders and containers are currently in use, but many of them either do not involve sanitizing or disinfecting the sponge, or they require complex sanitizing mechanisms which too narrowly restrict the dimensions and type of sponges which can be used compatibly with these sanitizing containers.

SUMMARY OF THE INVENTION

The invention disclosed herein, the sanitizing sponge container, provides a simple, inexpensive, but effective means of storing and sanitizing both natural and synthetic sponges between uses. In particular, this sanitizing sponge container will comprise an approximately rectangular, square, elliptical, or circular mouthed bowl or crock, with essentially vertical sides, forming an open top container of sufficient depth to contain a sponge and enough disinfectant fluid to completely cover the sponge, when the sponge is pushed to the bottom of the bowl. In one preferred embodiment, a bowl lid comprising a downward directed shaft extending into a rectangular bowl is described. This downward directed lid shaft fits within a perimeter which is slightly less than the inner perimeter of the bowl mouth, thus allowing this section of the lid to fit into the bowl in order to press downward on the sponge to be disinfected, keeping the sponge totally submerged in the disinfectant fluid during limited storage periods. Also included in this embodiment are two relatively open, flat, rectangular ribbed grates which fit horizontally into these bowls, these grates also having small knobs at their corners. These grates may be loose or one may be attached to the floor of the bowl and the other may be attached to the bottom surface of the lid shaft. The flat faces of these grates are held slightly away from the bowl bottom and the bottom surface of the lid shaft by these corner knobs. The sponge being sanitized is held between these grates and the spacing allows most of the sponge surface to come in contact with the disinfectant fluid.

In another preferred embodiment, the lid fits over the top edge of the mouth of the bowl and rests on the bowl rim. A grate is also provided on the bowl bottom in this embodiment. The central circular region of the top of this lid is provided with an open screw threaded collar into which a matching, screw threaded bolt is inserted which can be turned downward into the bowl and onto the sponge, forcing the sponge being disinfected onto the grate at the bottom of the bowl and holding it there under the disinfectant fluid.

The bowl, lid, grates and bolt, if present, may be manufactured out of a metal, ceramic, glass or plastic material, but other materials, compatible with the disinfectant and sponge composition could also be used.

Although this invention is directed primarily to storing and disinfecting sponges, it is obvious that with proper modifications, it could be applied to storing and disinfecting other wiping materials such as brushes and mops. For brevity, the disclosure will be limited to describing the invention in relation to storing and disinfecting sponges.

It is thus an object of this invention to provide a simple, inexpensive container means for storing or holding a sponge, while at the same time sanitizing, decontaminating and disinfecting the sponge in a disinfectant fluid.

It is a further object of this invention to provide a means for holding and sanitizing a sponge that can be used repeatedly while only requiring that the disinfectant fluid be changed as needed.

It is a further object of this invention to provide a sanitizing sponge container that can accommodate a variety of differently shaped and sized sponges.

These and other objects will be apparent to those skilled in the art

BRIEF DESCRIPTION OF THE DRAWINGS

The more specific object features and advantages of this invention will be more readily apparent from the following description, wherein reference is made to the accompanying drawings illustrating preferred embodiments of the invention.

In the drawings.

DETAILED DESCRIPTION OF THE DRAWINGS

The preferred embodiments are described here with respect to essentially rectangular open mouthed container bowls having essentially vertical side walls and their matching lids. It will be clear, however, from the description below, that many other shaped containers and lids could also be adapted to this application. In particular, the disclosure can easily be modified to describe square, circular or elliptical mouthed bowls or, in fact, generally bowls bounding convex interior volumes. Here, "convex" refers to bowl volumes such that any two interior points can be connected by a straight line lying entirely within the interior volume of the bowl. Some non convex shaped containers might also be used, but they would be less accommodating for certain sponge shapes.

Figure 1:
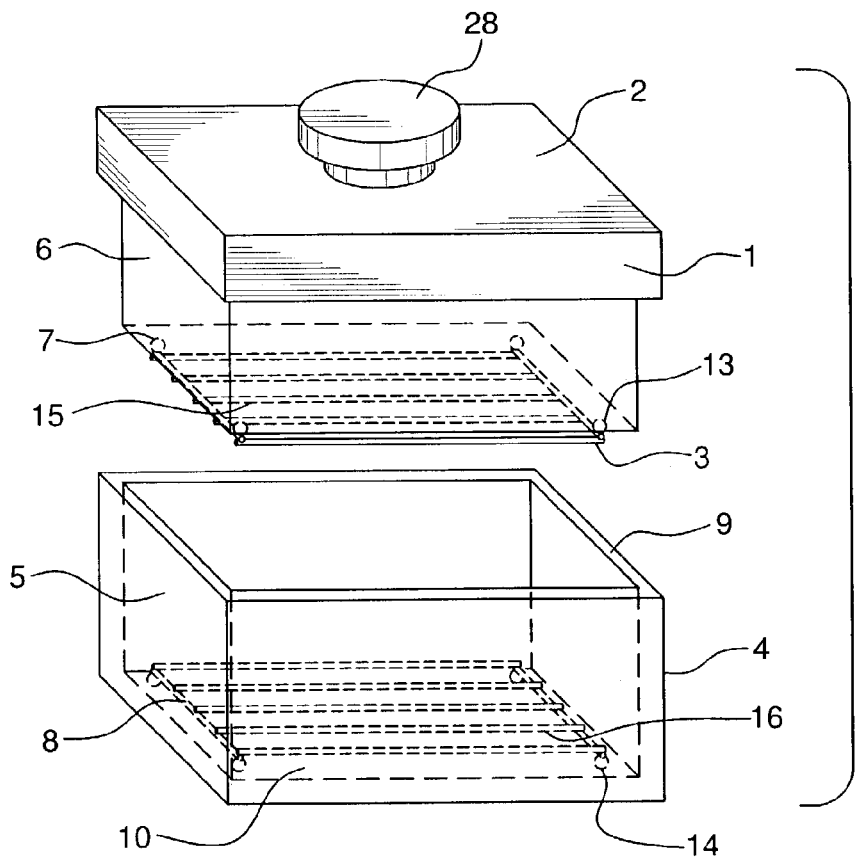
FIG. 1 is a perspective view of a first embodiment of a sanitizing sponge container with the lid suspended above a rectangular container bowl and the grates in place.

Referring to the figures, FIG. 1 is a perspective view of an essentially rectangular, open mouthed sanitizing sponge container bowl 4, with its lid 1 suspended above it. The side walls 5 of the container bowl 4 are essentially vertical. Positioned above the container bowl 4, is the container lid 1, having a centrally positioned raised knob 28 on its rectangular top surface slab 2 to facilitate lifting and lowering the lid 1. The underside of the top surface slab 2 of the lid 1 has a downward projecting rectangular block shaft 6 with vertical lateral walls. The bottom of the lid shaft 6 is a flat, rectangular surface 7, which is dimensioned to allow the shaft 6 to fit downward into the container bowl 4 in order to press down onto the top surface of a submerged sponge (not shown). To the bottom surface 7 of the shaft 6, is attached a downward facing, generally open, rectangular ribbed grate 3, see also FIGS. 2 and 3. The grate 3 comprises a rectangular, open frame with several parallel ribs 15 connecting at least two of the opposite sides of the frame 3. At each of the four corners of the grate 3 is a small upward projecting knob 13, which holds the plane of the grate 3 slightly away from the bottom surface 7 of the shaft 6, in order to allow exposure of most of the upper surface of the sponge to the disinfectant fluid, when the shaft 6 is pressing down on the sponge. This is indicated in FIG. 2, where the lid 1 is lowered so that the shaft 6 has partially entered the mouth of the container bowl 4.

Figure 2:
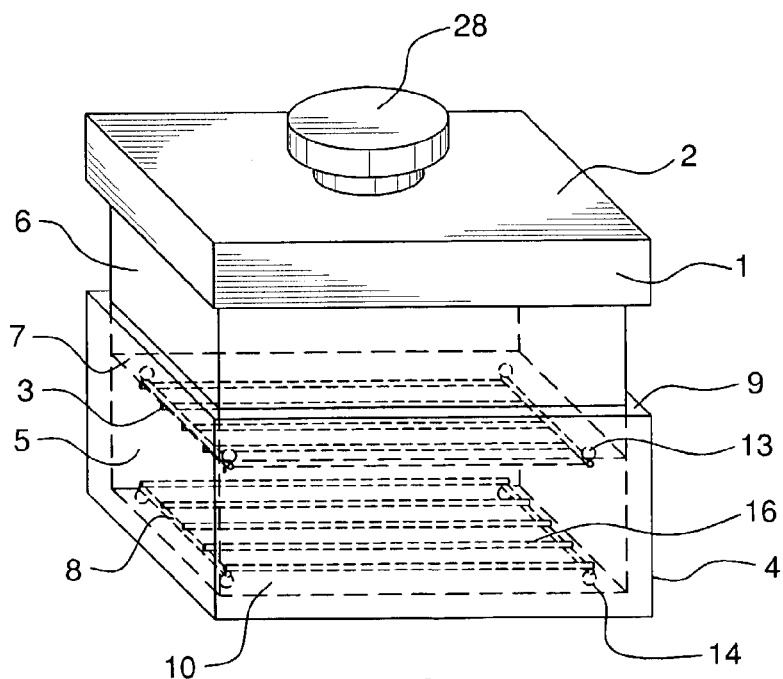
FIG. 2 is a perspective view of the closed sponge container of FIG. 1 with the grates in place.
Figure 4:
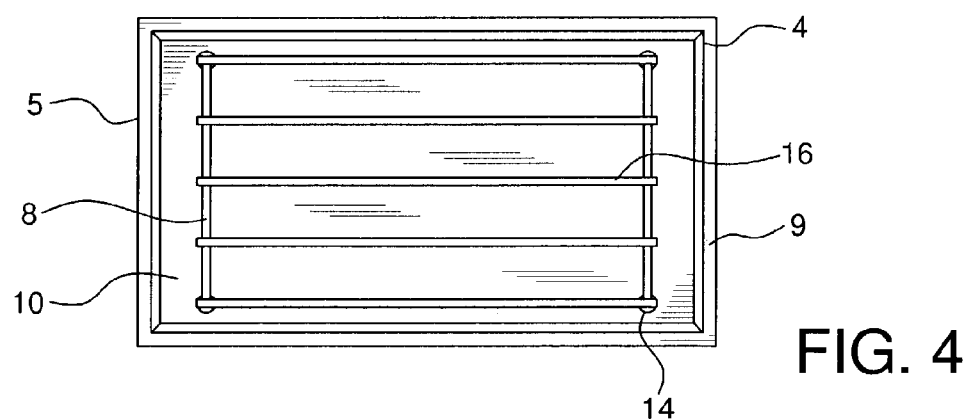
FIG. 4 is a plan view of the interior container bowl floor with a grate in place.
Figure 5:
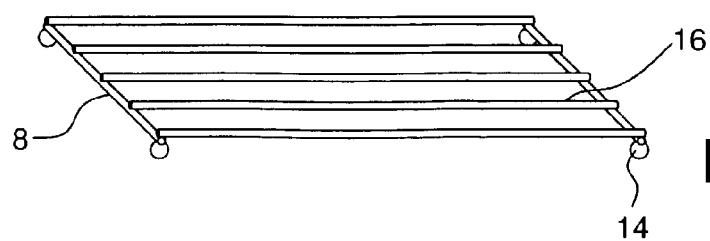
FIG. 5 is a perspective view of a grate in the container bowl floor position.

As also shown in FIGS. 1, 2, and 4, attached to or resting on the essentially planar interior floor 10 of the container bowl 4, is an upward facing rectangular ribbed grate 8, having parallel ribs 16 connecting at least two opposite sides of the grate 8. The grate 8 is supported, at each of its corners, by a small downward projecting knob 14. These knobs 14 hold the ribbed section of the grate 8 slightly above the floor 10 of the container bowl 4, in order to allow the disinfectant fluid to make contact with most of the bottom surface of a sponge (not shown), being pressed onto the grate 8 by the lid shaft 6, see FIG. 5 also.

As shown in FIGS. 1, 2, 3, 4 and 5, the grates 3 and 8 bound horizontal areas that are less than the area of the interior container bowl floor 10 and are identical to each other in this embodiment, but are positioned upside down to each other. This embodiment is easily modified to allow the option of using loose grates rather than having them attached to the lid 1 and the container bowl 4. Grates may be easier to clean if they are loose rather than if they are attached.

Figure 3:
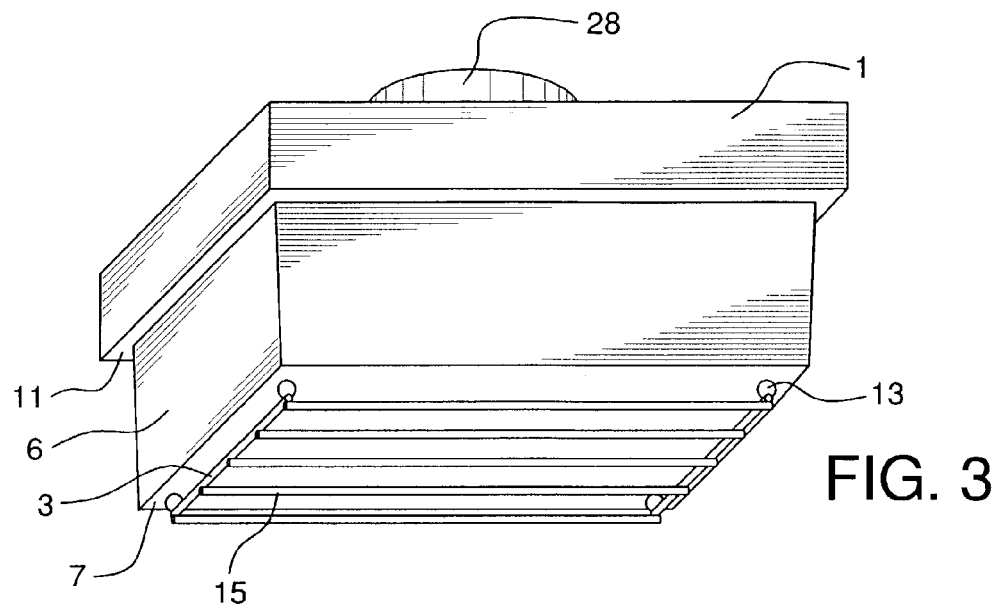
FIG. 3 is an upward directed perspective view of the lid of FIG. 1 across its bottom surface with the grate attached.

The dimensions of the horizontal perimeter of the top surface of the slab 2 of the lid 1 are slightly greater than the inner perimeter of the mouth of the container bowl 4. This prevents the lid 1 from being lowered so far into the container bowl 4 that it causes an overflow of disinfectant fluid. Instead, at its maximum lowered position, the underside border 11 of the slab 2 of the lid 1, as shown in FIG. 3, will rest on the rim 9 of the container bowl mouth, see FIGS. 1, 2 and 4.

The container bowl 4 and the lid 1 are to be manufactured of solid, thick walled, easily cleaned, preferably transparent material such as glass, ceramic, or plastic compatible with the sponges and disinfectant fluid. The natural weight of the lid may be sufficient to hold down a sponge under the disinfectant fluid in the bowl 4, so that no additional weighting is necessary. Otherwise, additional weight can be added to the lid 1 as needed.

The grates 3 and 8 are to be manufactured of a non-corroding metal, ceramic or plastic material compatible with the sponges and disinfectant fluid.

Figure 6:
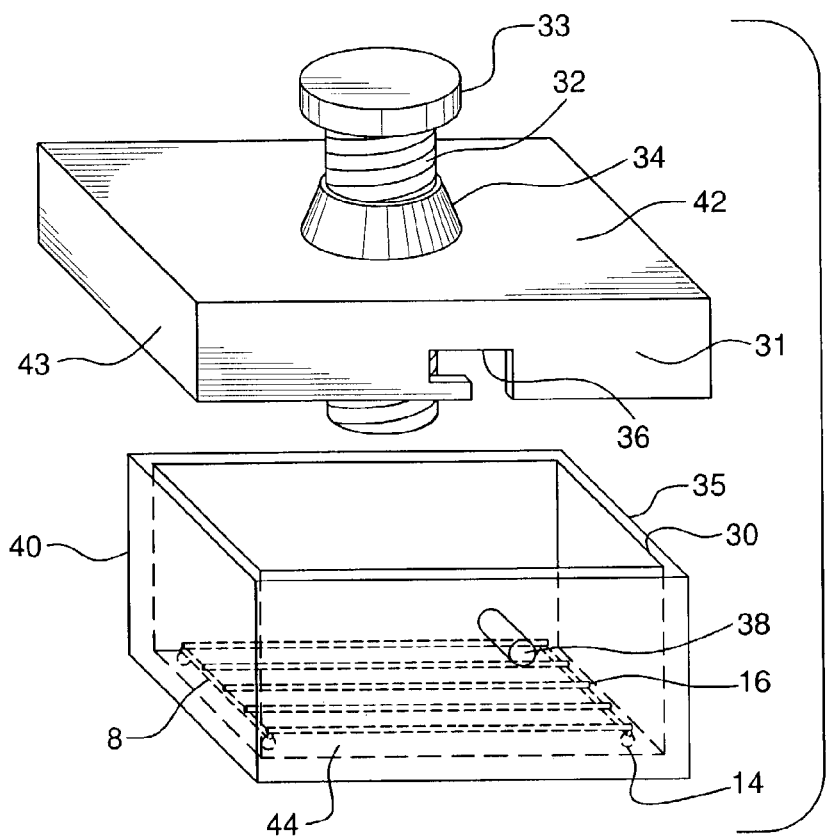
FIG. 6 is a perspective view of a second embodiment of a sanitizing sponge container with the lid containing the bolt suspended above a rectangular container bowl and a grate in place in the bowl.
Figure 7:
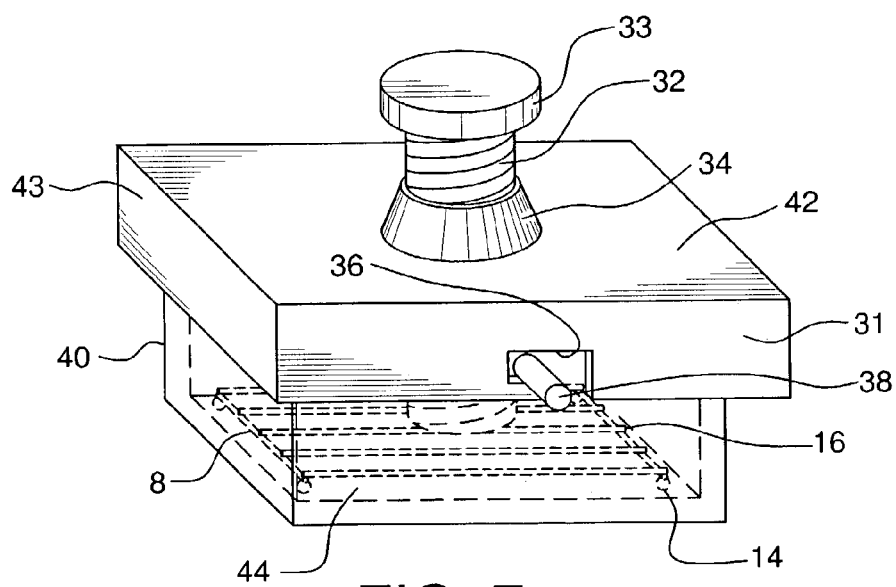
FIG. 7 is a perspective view of the closed sanitizing sponge container of FIG. 6.
Figure 8:
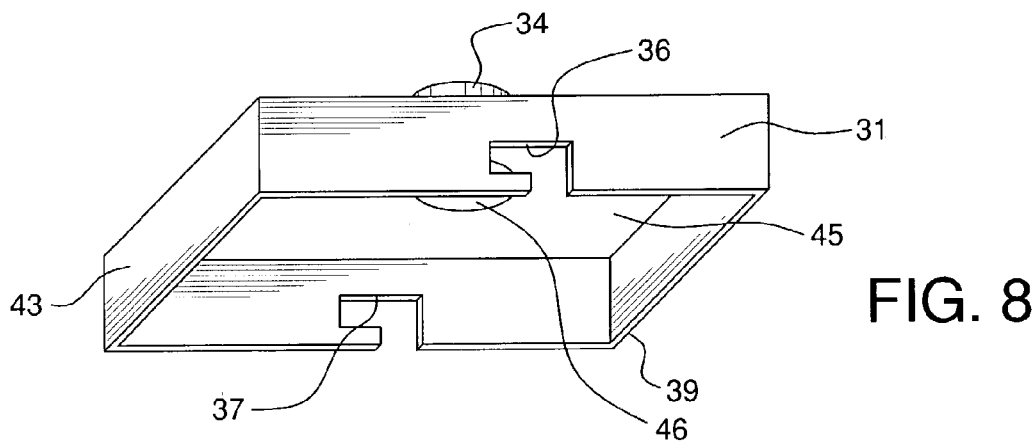
FIG. 8 is an upward directed perspective view of the lid of FIG. 6 across its downward facing inside surface.
Figure 9:
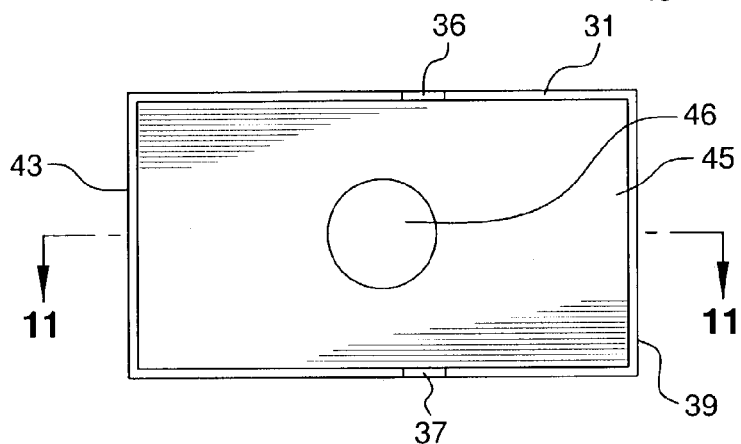
FIG. 9 is a bottom view of the underside of the lid of FIG. 8.
Figure 10:
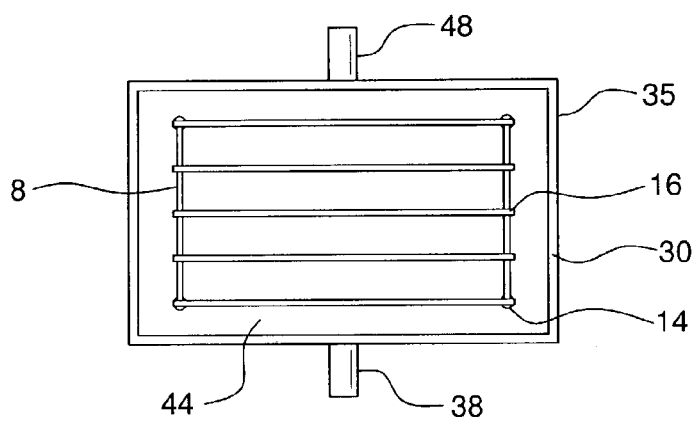
FIG. 10 is a plan view of the interior of the container bowl of FIG. 6 with the grate in place.
Figure 11:
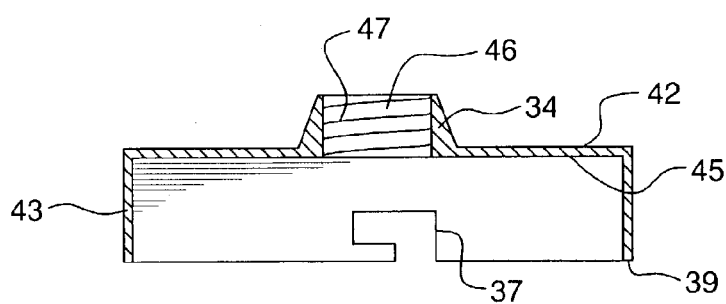
FIG. 11 is an elevation cross section view of the lid cut along the line 11 of FIG. 9.

Referring now to FIGS. 6 and 7, a second preferred embodiment of the sanitizing sponge container is presented in perspective view, comprising a fluid container bowl 35 having an essentially flat planar interior floor 44 of horizontal rectangular cross section and four essentially vertical, upward directed side walls 40, and a matching rectangular lid 31. The flat outer roof 42 of the lid 31 meets four downward directed essentially vertical side walls 43, see FIGS. 6, 7, 8 and 11. In FIG. 6, the lid 31 is shown suspended above the bowl 35 and in FIG. 7, the lid 31 is shown atop the bowl 35. The lengths of the sides of the inner perimeter of the inner lid roof 45 are slightly greater than the lengths of the side walls 40 of the outer perimeter of the mouth of the bowl 35, see FIGS. 7, 8, 9 and 10. This allows the inner roof 45 of the lid 31 to rest atop the rim 30 of the bowl 35 when the lid 31 is lowered completely onto the bowl 35 as in FIG. 7. As indicated in FIGS. 6, 7 and 10, the inner surface of the floor 44 of the bowl 35 may be provided with the open rectangular grate 8 as described in the first embodiment of the sanitizing sponge container. The grate having parallel ribs 16 and small lift knobs 14 at the corners, see FIGS. 6, 7 and 10. The grate 8 is provides a means to hold a sponge off the floor 44 of the bowl 35 exposing the bottom surface of the sponge (not shown) to the disinfectant fluid in the bowl 35.

Referring now to FIGS. 6, 7, 8, 9 and 11, the lid 31 is further comprises an upward projecting neck 34, having a circular horizontal cross section provided with a vertical circular aperture 46, passing through the neck 34 and the roof 42 of the lid 31, and having screw threads 47. The vertical axis of this aperture 46 is aligned with the centroid of the surface of the roof 42 of the lid 31. Screwed downward through this aperture 46 is a matching threaded cylindrical bolt 32, having a diameter of approximately one-half inch or more, see FIGS. 6 and 7. When the bowl 35 contains disinfectant fluid and a sponge to be disinfected, the lid 31 is placed over and down atop the rim 30 of the bowl 35, and the bolt 32 is turned downward through the aperture 46 into the bowl 35 and onto the top of the sponge, to force the sponge downward into the disinfectant fluid and against the grate 8 on the bottom of the bowl 35. Across the top of the bolt 32 is a flat circular cylindrical head 33. This head 33 provides a finger or hand grip and extra radial torque to facilitate turning the bolt 32, see FIGS. 6 and 7.

In order to limit the upward movement of the lid 31, when the bolt 32 is being turned downward against a sponge, and to provide an increased bracing force for the bolt 32, the lid is provided with two inverted L-shaped slots 36 and 37 on opposite vertical sidewalls 43 of the lid 31, a channel segment of each slit being open vertically downward through the bottom rim 39 of the lid 31, see FIGS. 6, 7, 8, 9 and 11. To be mated with these slots 36 and 37 are two horizontally outward extending narrow peg-like protrusions 38 and 48, on the matching opposite side walls of the bowl 35, that fit into the open ends of the slots 36 and 37, see FIGS. 6, 7, 8, 9, 10 and 11. When the lid 31 is placed down onto the rim 30 of the bowl 35, the lid is shifted forward or backward so that slots 36 and 37 engage the pegs 38 and 48 and allow the lid to rest on the rim 30 of the bowl 35. The lid 31 is then shifted forward or backward so that these pegs now extend outward over the lower closed edges of the slots. Thus, when the bolt 32 is turned downward against a sponge on the grate 8 on the floor 44 of the bowl 35, the lid 31 will rise until the pegs 38 and 48 are braced against the bottom edges of the slots 36 and 37, holding the lid 31 and bowl 35 in rigid equilibrium see, in particular, FIG. 7. The lateral length of the inner roof 45 of the lid 31 must, therefore, be of sufficient length to allow it to be shifted far enough to allow these slots and pegs to engage and disengage.

It should be noted, as in the first embodiment, that the grate 8 can be either attached to the bowl floor 44 or it can be separate and placed into the sanitizing bowl 35 when required.

Instead of grates, the surfaces of the sanitizing container, in contact with the sponge surfaces, could be contoured with ridges, ribs and nipples in order to provide more exposed areas on the sponge to make contact with the disinfectant fluid, when the sponge is pushed to the bottom of the bowl.

Also, the design of the lids and container bowls can be modified to allow the lids to be attached to the container bowls by hinges, instead of being unattached as in the preferred embodiments presented here.

The same considerations with regard to the choice of manufacturing materials apply to the second preferred embodiment as in the first embodiment.

It will be understood that the above description of the present invention is susceptible to various modifications, changes and adaptations, and the same are intended to be comprehended within the meaning and range of equivalents of the appended claims.

I claim:

1. A sanitizing sponge container comprising a fluid container bowl, open at the top, having an essentially planar interior floor and side walls of sufficient height to allow said container bowl to hold, in its interior, various shaped and sized sponges and sufficient disinfectant fluid to completely submerge said sponges, said sanitizing sponge container further comprising an essentially flat matching lid, said lid having extended from its bottom surface a downward projecting lid shaft, said shaft being dimensioned to fit downward into said container bowl, said shaft also being of vertical length less than the depth of said container bowl, allowing said shaft to fit downward into said container bowl and force downward a sponge being sanitized in said container bowl, said lid having sufficient weight to hold a sponge completely submerged under said disinfectant fluid, said container bowl lid further comprising a spacing means to hold said downward facing surface of said lid shaft above said top surface of said sponge, while said lid shaft holds said sponge completely submerged under the disinfectant fluid in said container bowl, and wherein said spacing means comprises an essentially horizontal, flat, rectangular, ribbed grate which fits horizontally into the interior of said bowl and across the bottom surface of said lid shaft, said grate further comprising an upward projecting knob at each corner of said grate.

2. The container bowl of claim 1, further comprising spacing means on said interior floor of said container bowl, provided to hold the bottom surfaces of said sponges above said container bowl interior floor.

3. The container bowl of claim 2, wherein said support means on said interior container bowl floor comprises an essentially horizontal, flat, rectangular, open, ribbed grate having a downward projecting knob at each corner of said grate, said grate bounding a horizontal surface area and shape which fits horizontally into said interior area of said container bowl floor, said grate being raised above said interior container bowl floor by said corner knobs resting on said container bowl floor.

4. The container bowl of claim 3, wherein said grate comprises a rectangular, bounding, horizontal frame further comprising at least two opposite edges connected by a multiplicity of parallel ribs.

5. The grate of claim 1, wherein said grate comprises a rectangular bounding frame, said frame further comprising at least two opposite edges connected by a multiplicity of parallel ribs.

6. A sanitizing sponge container comprising a fluid container bowl, open at the top, said bowl having a convex horizontal cross section with an essentially planar bottom interior floor, essentially vertical side walls of sufficient height to allow said container bowl to hold, in its interior, various shaped and sized sponges, and sufficient disinfectant fluid to completely submerge said sponges, and said bowl further comprising a separate matching lid to close said bowl, said lid comprising an essentially flat, planar outer upper surface of similar shape to match the perimeter of said open container bowl mouth, said lid further comprising essentially vertical downward directed side walls bounding the perimeter of said lid, the perimeter of the inner lateral surface of said lid to be slightly greater than the outer perimeter of said rim of said container bowl, and the vertical height of said side walls of said lid to be sufficiently less than the height of said vertical side walls of said container bowl to allow said lid to be lowered over and onto said container bowl and to rest on said rim of said bowl, closing said bowl, said lid further comprising a circular screw threaded aperture axially aligned with the planar centroid of said upper surface of said lid, and said lid further comprising a matching circular, cylindrical, threaded bolt fitting said aperture and of sufficient length to reach to bottom of said bowl when said lid is resting on said rim of said bowl, and said bolt is screwed downward through said aperture into said bowl onto a submerged sponge, wherein said container bowl and said lid have geometrically similar rectangular horizontal cross sections, with that of the interior of said lid being greater than that across the mouth of said container bowl, said container bowl further comprising a support means, on said interior floor of said container bowl, to hold the bottom surface of said sponges above said container bowl interior floor when said sponges are submerged, and wherein said support means, on said interior floor of said container bowl, comprises an essentially horizontal, flat, rectangular ribbed grate, said grate further comprising a downward projecting knob at each corner of said grate, said grate further having a horizontal surface area and shape which fits into said interior floor area of said container bowl, said grate being raised slightly above said floor by said corner knobs resting on said interior floor.

7. The sanitizing sponge container of claim 6, further comprising a complementary latching means on said bowl and said lid, to limit the upward movement of said lid when said bolt is screwed downward into said bowl.

8. The container bowl of claim 6, wherein said grate comprises a rectangular bounding frame, said frame further comprising at least two opposite edges connected by a multiplicity of parallel ribs.

* * * * *